United States Patent
Park et al.

(10) Patent No.: US 9,523,118 B2
(45) Date of Patent: Dec. 20, 2016

(54) METHOD OF DETECTING NUCLEIC ACIDS CONTAINING A GENETIC VARIATION

(71) Applicant: Samsung Electronics Co., Ltd., Suwon-si, Gyeonggi-do (KR)

(72) Inventors: Dong-hyun Park, Chuncheon-si (KR); Yeon-jeong Kim, Yongin-si (KR); Kyung-yeon Han, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 131 days.

(21) Appl. No.: 14/189,762

(22) Filed: Feb. 25, 2014

(65) Prior Publication Data

US 2015/0031023 A1 Jan. 29, 2015

(30) Foreign Application Priority Data

Jul. 23, 2013 (KR) .................. 10-2013-0086968

(51) Int. Cl.
*C12Q 1/68* (2006.01)

(52) U.S. Cl.
CPC .................. *C12Q 1/6858* (2013.01)

(58) Field of Classification Search
None
See application file for complete search history.

(56) References Cited

U.S. PATENT DOCUMENTS

| | | | |
|---|---|---|---|
| 2008/0176226 A1 | 7/2008 | Chiou et al. | |
| 2010/0143882 A1* | 6/2010 | van de Wiel | C12Q 1/6865 435/5 |
| 2010/0285478 A1* | 11/2010 | Chen | C12Q 1/6858 435/6.14 |
| 2012/0032211 A1 | 2/2012 | Schindler et al. | |
| 2012/0088275 A1* | 4/2012 | Wangh | C12Q 1/6806 435/91.2 |
| 2014/0377762 A1* | 12/2014 | Kelly | C12Q 1/6858 435/6.12 |

FOREIGN PATENT DOCUMENTS

| | | | |
|---|---|---|---|
| JP | 2006-288353 A | 10/2006 | |
| JP | 2006-304611 A | 11/2006 | |
| KR | 10-2011-0042511 A | 4/2011 | |
| KR | 10-2011-0119512 A | 11/2011 | |
| WO | WO 2011/105732 A2 | 9/2011 | |
| WO | WO 2012095639 A2 * | 7/2012 | ........... C12Q 1/6827 |

OTHER PUBLICATIONS

Li et al. (A new class of homogeneous nucleic acid probes based on specific displacement hybridization, Nucleic Acids Res. Jan. 15, 2002; 30(2): e5).*

Oh et al., Detection of low-level KRAS mutations using PNA-mediated asymmetric PCR clamping and melting curve analysis with unlabeled probes, J Mol Diagn. Jul. 2010;12(4):418-24. Epub Apr. 22, 2010.*

Thiede, et al. Simple and sensitive detection of mutations in the ras proto-oncogenes using PNA-mediated PCR clamping, *Nucleic Acids Research*, 24(5): 983-984 (1996).

* cited by examiner

*Primary Examiner* — Aaron Priest

(74) *Attorney, Agent, or Firm* — Leydig, Voit & Mayer, Ltd.

(57) ABSTRACT

Provided are a composition or a kit for detecting a nucleic acid with genetic variation including a first amplification blocking nucleic acid and a second amplification blocking nucleic acid, and a method of detecting a nucleic acid with genetic variation by using the same. Based on the above, a nucleic acid with genetic variation can be detected with high sensitivity and accuracy.

14 Claims, 2 Drawing Sheets

AMPLIFICATION

METHOD OF DETECTING NUCLEIC ACIDS CONTAINING A GENETIC VARIATION

CROSS-REFERENCE TO RELATED APPLICATIONS

This application claims the benefit of Korean Patent Application No. 10-2013-0086968, filed on Jul. 23, 2013, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,686 Byte ASCII (Text) file named "715480_ST25.TXT," created on Feb. 24, 2014.

BACKGROUND

1. Field

The present disclosure relates to a composition and a kit for detecting a nucleic acid with genetic variation, and a method of detecting a nucleic acid with genetic variation by using the same.

2. Description of the Related Art

Molecular diagnostic methods have been widely used in the fields of medicine, identification, the environment, etc. Detection of a variant of a specific nucleic acid sequence can provide information regarding polymorphism or mutations including disease-related mutations.

Numerous methods of detecting the presence of disease-related genetic variations or specific genotypes have been developed and used. Examples of the methods include direct sequencing, allele-specific PCR, Restriction Fragment Length Polymorphism (RFLP), Taqman™ probe technique, amplification refractory mutation system (ARMS)-PCR, denaturing HPLC (dHPLC), and real-time PCR, etc. Major factors considered in detecting genetic variations are sensitivity, which enables detection of mutant DNA present at a low rate in normal DNA, and specificity, which enables minimalization of the rate of false positive, i.e., the rate of normal DNA being falsely determined as mutant DNA.

However, the existing methods have not been successful in showing a high reliability level of sensitivity and specificity. For example, the direct sequencing method has the advantage of having a relatively low rate of false positives due to high specificity but it has the disadvantage of enabling detection only when at least about 20 to about 30% of mutant DNA is present in a given sample.

Thus, there is a desire for a method that is capable of detecting with high sensitivity and accuracy even when the frequency of nucleic acids with genetic variation is low.

SUMMARY

Provided are compositions for detecting nucleic acids with genetic variation including a first amplification blocking nucleic acid and a second amplification blocking nucleic acid. In some embodiments, the first amplification blocking nucleic acid is a polynucleotide whose sequence is the same as or complementary to at least two consecutive nucleotides of a region of a wild type gene known to have genetic variation, and the second amplification blocking nucleic acid is a polynucleotide whose sequence is complementary to at least two consecutive nucleotides of the first amplification blocking nucleic acid.

Provided are kits for detecting nucleic acids with genetic variation including a first amplification blocking nucleic acid, a second amplification blocking nucleic acid, a primer pair, and a nucleic acid polymerase. In particular, provided are kits for detecting a nucleic acid with genetic variation comprising a first amplification blocking nucleic acid, a second amplification blocking nucleic acid, a primer pair, and a nucleic acid polymerase, wherein the first amplification blocking nucleic acid is a polynucleotide whose sequence is the same as or complementary to at least two consecutive nucleotides of a region of a wild type gene known to have genetic variation, and the second amplification blocking nucleic acid is a polynucleotide whose sequence is complementary to at least two consecutive nucleotides of the first amplification blocking nucleic acid.

Also provided is a method of detecting a nucleic acid with genetic variation. In one embodiment, the method comprises: (a) incubating a sample including a target nucleic acid comprising a region of a wild type gene known to exhibit genetic variation with a primer pair; a first amplification blocking nucleic acid comprising a sequence that is the same as or complementary to at least two consecutive nucleotides of the region of the wild type gene known to exhibit genetic variation; and a second amplification blocking nucleic acid comprising a sequence complementary to at least two consecutive nucleotides of the first amplification blocking nucleic acid; (b) amplifying the target nucleic acid with a polymerase; thereby producing an amplification product; and (c) detecting the amplification product to detect a nucleic acid with genetic variation.

In another embodiment, the detection method comprises: (a) incubating a sample including a target nucleic acid comprising a region of a wild type gene known to exhibit genetic variation with a first primer pair and a first amplification blocking nucleic acid, wherein the first amplification blocking nucleic acid comprises a sequence that is the same as or complementary to at least two consecutive nucleotides of the region of the wild type gene known to exhibit genetic variation; (b) amplifying the target nucleic acid with a nucleic acid polymerase to provide a first amplification product; (c) incubating the first amplification product with a second primer pair and a second amplification blocking nucleic acid, wherein the second amplification blocking nucleic acid comprises a sequence complementary to at least two consecutive nucleotides of the first amplification blocking nucleic acid; (d) amplifying the first amplification product with a nucleic acid polymerase to provide a second amplification product; and (e) detecting the second amplification product to detect a nucleic acid with genetic variation.

BRIEF DESCRIPTION OF THE DRAWINGS

These and/or other aspects will become apparent and more readily appreciated from the following description of the embodiments, taken in conjunction with the accompanying drawings in which:

FIG. 1 includes FIG. 1a and FIG. 1b.

DESCRIPTION

Figure 1A:
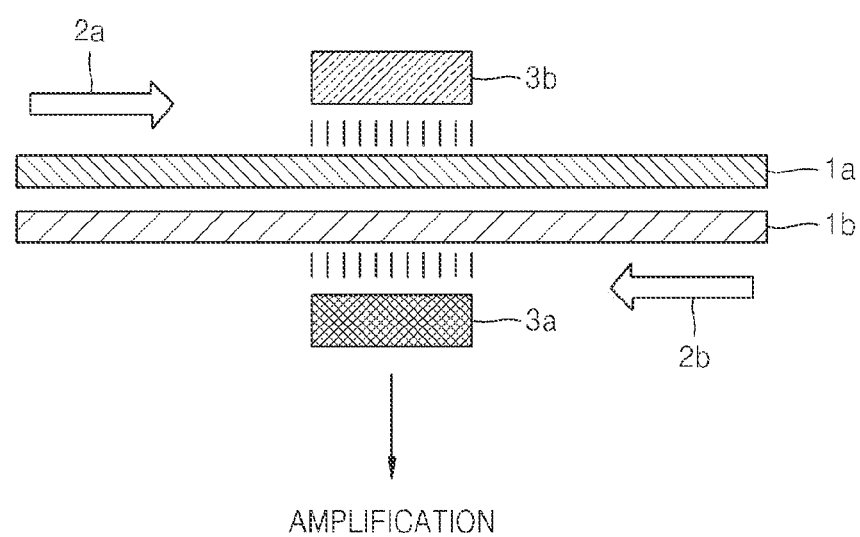
FIG. 1a depicts a method of detecting a nucleic acid with genetic variation, according to an exemplary embodiment of the present invention.
Figure 1B:
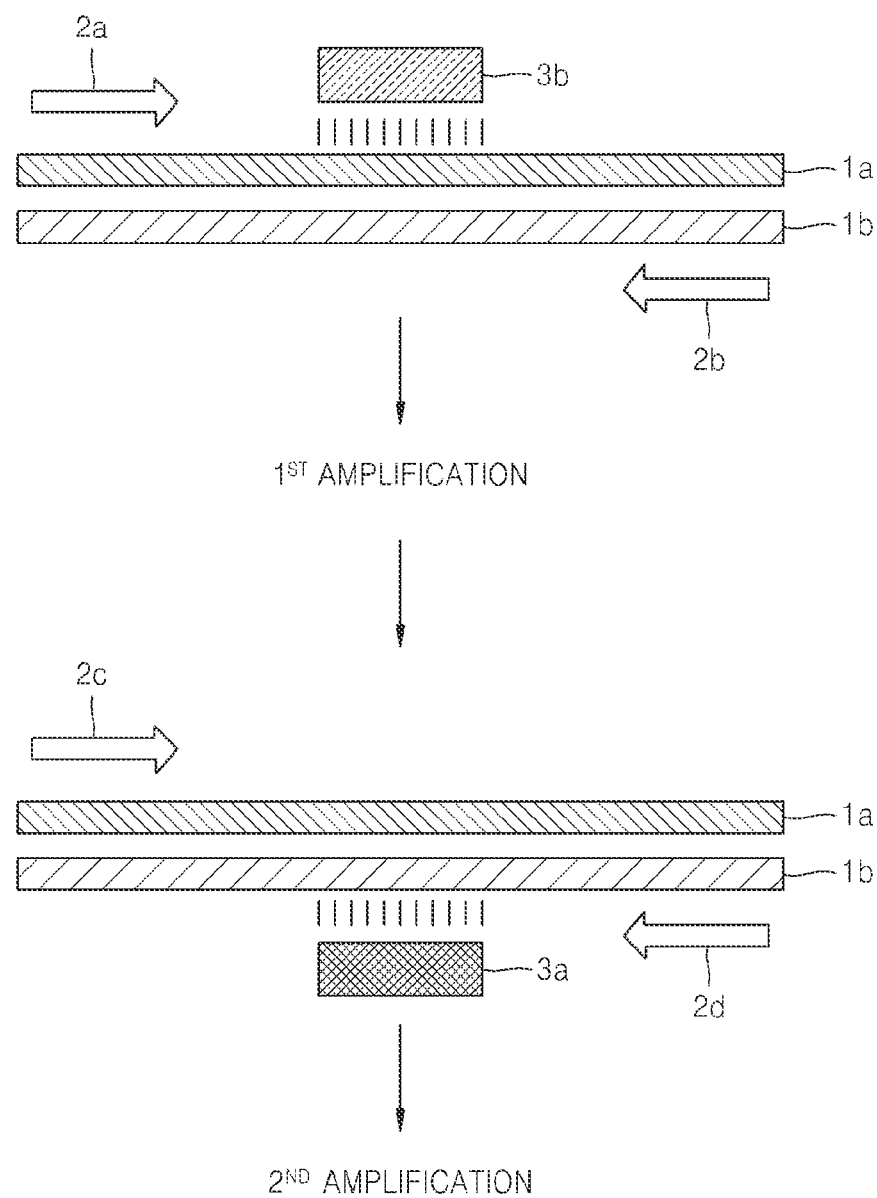
FIG. 1b depicts a method of detecting a nucleic acid with genetic variation, according to another exemplary embodiment of the present invention (1a denotes a sense strand, 1b denotes an anti-sense strand, 2a and 2c denote forward primers, 2b and 2d denote a reverse primer, 3a denotes a sense blocker, and 3b denotes an anti-sense blocker).

Additional aspects will be set forth in part in the description which follows and, in part, will be apparent from the description, or may be learned by practice of the presented embodiments.

According to an aspect of the present invention, there is provided a composition for detecting a nucleic acid with genetic variation comprising, consisting of, or consisting essentially of a first amplification blocking nucleic acid and a second amplification blocking nucleic acid. The first amplification blocking nucleic acid is a polynucleotide whose sequence is the same as or complementary to at least two consecutive nucleotides of a region of a wild type gene known to have genetic variation. The second amplification blocking nucleic acid is a polynucleotide whose sequence is complementary to at least two consecutive nucleotides (for example, 2 nucleotides (hereinafter, "nt"), 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, or more) of the first amplification blocking nucleic acid.

As used herein, "wild type gene" refers to a nucleotide which is most common in nature or any nucleotide assigned as normal.

As used herein, "region with genetic variation" refers to a region which includes genetic variation to be detected. Genetic variation refers to a variation that occurs due to a conversion or change in genetic composition. The genetic variation may be an allele, a Single Nucleotide Polymorphism (SNP), a mutation, or combinations thereof. An allele is an alternative form of a gene which expresses a different phenotype while occupying the same locus of a given chromosome. An allele also refers to a gene which has a different nucleotide sequence while occupying the same locus in a homologous chromosome. A mutation may include a point mutation, a transition mutation, a transversion mutation, a missense mutation, a nonsense mutation, a duplication, a deletion, an insertion, a translocation, an inversion, or combinations thereof. SNP refers to a variation in one or a few nucleotides of a genomic sequence reflecting variations among individuals.

As used herein, "amplification blocking nucleic acid" may be interchangeably used with the term "blocker." An amplification blocking nucleic acid cannot be elongated by a nucleic acid polymerase, and, therefore, cannot serve as a primer for PCR. When the amplification blocking nucleic acid binds to a complementary sequence on a target, the blocking nucleic acid prevents amplification of the sequence of the target to which it is bound. The first amplification blocking nucleic acid may be a polynucleotide that is the same as or complementary to a nucleotide of at least two consecutive nucleotides comprising a nucleotide sequence of a wild type gene corresponding to a region with genetic variation in a nucleotide sequence of a wild type nucleic acid of a sample. The second amplification blocking nucleic acid may be a polynucleotide that is the same as or complementary to a nucleotide of at least two consecutive nucleotides comprising a nucleotide sequence of a wild type gene corresponding to a region with genetic variation in a nucleotide sequence of a wild type nucleic acid of a sample, and complementary to the nucleotide of at least two consecutive nucleotides of the first amplification blocking nucleic acid.

The first amplification blocking nucleic acid and/or the second amplification blocking nucleic acid may include DNA, RNA, Peptide Nucleic Acid (PNA), Locked Nucleic Acid (LNA), Zip Nucleic Acid (ZNA), Bridged Nucleic Acid (BNA), a nucleotide analogue, or combinations thereof.

The first amplification blocking nucleic acid and/or the second amplification blocking nucleic acid may be chemically modified. For example, the first amplification blocking nucleic acid and/or the second amplification blocking nucleic acid may include a nucleic acid in which a hydroxyl group at its 3' terminus is removed, an inverted nucleotide, or a dideoxynucleotide.

The first amplification blocking nucleic acid and/or the second amplification blocking nucleic acid may have a length in a range of about 5 nt to about 30 nt. For example, the length of the nucleic acid may be from about 7 nt to about 27 nt, about 9 nt to about 24 nt, about 9 nt to about 15 nt, about 9 nt to about 13 nt, about 11 nt to about 13 nt, about 13 nt to about 24 nt, about 13 nt to about 21 nt, and about 13 nt to about 17 nt.

The melting temperature of the first amplification blocking nucleic acid and/or the second amplification blocking nucleic acid may be in a range of about 50° C. to about 80° C. For example, the melting temperature of the first amplification blocking nucleic acid or the second amplification blocking nucleic acid may be from about 55° C. to about 80° C., about 55° C. to about 75° C., about 60° C. to about 75° C., or about 60° C. to about 70° C. The melting temperature of the first amplification blocking nucleic acid and/or the second amplification blocking nucleic acid may be higher than that of the primer. For example, the melting temperature of the first amplification blocking nucleic acid and/or the second amplification blocking nucleic acid may be higher than that of the primer by from about 1° C. to about 30° C., about 3° C. to about 30° C., about 5° C. to about 30° C., about 7° C. to about 30° C., about 10° C. to about 30° C., about 13° C. to about 30° C., about 15° C. to about 30° C., about 17° C. to about 30° C., about 20° C. to about 30° C., about 23° C. to about 30° C., or about 25° C. to about 30° C.

The composition for detecting nucleic acids may be a composition for detecting nucleic acids by amplifying nucleic acids. As used herein, "amplification", refers to an increase in the copy number of a nucleic acid, including generation of DNA from RNA. The method of amplifying nucleic acids may be any known method of amplification. Accordingly, the composition may further include a known material required for the amplification of nucleic acids. For example, the composition may further include a nucleic acid polymerase, a buffer for the activation of nucleic acid polymerase, a cofactor, and/or a substrate.

In an aspect of the present invention, there is provided a kit for detecting a nucleic acid with genetic variation including a first amplification blocking nucleic acid, a second amplification blocking nucleic acid, a primer pair, and a nucleic acid polymerase. As described above, the first amplification blocking nucleic acid is a polynucleotide that is the same as or complementary to a nucleotide of at least two consecutive nucleotides comprising a nucleotide sequence of a wild type gene corresponding to a region with genetic variation in a nucleotide sequence of a wild type nucleic acid of a sample. The second amplification blocking nucleic acid is a polynucleotide that is the same as or complementary to a nucleotide of at least two consecutive nucleotides comprising a nucleotide sequence of a wild type gene corresponding to a region with genetic variation in a nucleotide sequence of a wild type nucleic acid of a sample, and complementary to the nucleotide of at least two consecutive nucleotides of the first amplification blocking nucleic acid.

The primer pair comprises, consists essentially of, or consists of a forward primer and a reverse primer. The primer refers to a short strand of nucleotides which serves as a starting point for template-dependent nucleic acid synthesis. The primer also refers to a nucleotide having a sequence complementary to the 3' terminal region of any one of a sense strand and an anti-sense strand of target nucleic acid sequences. The sense strand refers to a strand of nucleic acid sequences to be targeted. For example, the sense strand may have the same sequence as that of mRNA. The anti-sense strand refers to a strand complementary to the sense strand. For example, the anti-sense strand may be a template for mRNA synthesis. The forward primer is a primer complementary to the anti-sense strand. For example, the forward primer may include nucleotides whose sequence is the same as at least two consecutive nucleotides at the 5' terminal region of nucleic acid sequences to be amplified. The reverse primer is a primer complementary to the sense strand. For example, the reverse primer may include nucleotides whose sequence is the same as at least two consecutive nucleotides at the 3' terminal region of nucleic acid sequences to be amplified. The length of the primers may be from about 5 nt to about 30 nt, about 7 nt to about 30 nt, about 9 nt to about 30 nt, about 12 nt to about 30 nt, about 15 nt to about 30 nt, about 17 nt to about 27 nt, or about 20 nt to about 27 nt.

The primer pair may be specific to a strand comprising a nucleic acid with genetic variation or to a strand complementary to the same. The primer pair may include a nucleotide whose sequence is the same as or complementary to the nucleic acid with genetic variation.

The nucleic acid polymerase may be nucleic acid DNA polymerase, RNA polymerase, reverse transcriptase, or combinations thereof. DNA polymerase may be, for example, Taq DNA polymerase, Pfx DNA polymerase, Tfi DNA polymerase, Tth DNA polymerase, Tfl DNA polymerase, hot start polymerase, or combinations thereof. The RNA polymerase may be, for example, T7 RNA polymerase, or SP6 RNA polymerase. The reverse transcriptase may be, for example, Moloney Murine Leukemia Virus (MMLV) reverse transcriptase, Human Immunodeficiency Virus (HIV) reverse transcriptase, or Avian Myeloblastosis Virus (AMV) reverse transcriptase.

The kit may further include a known material required for the amplification of the target nucleic acid. For example, the kit may further include a buffer for the activation of nucleic acid polymerase, a cofactor, and/or a substrate. For example, the kit may further include a target nucleic acid. The kit may include a material required for reverse transcription or polymerase chain reaction (PCR) amplification. In addition, the kit may further include an instruction for the amplification of the target nucleic acid.

In another aspect of the present invention, there is provided a method of detecting a nucleic acid with genetic variation.

In one embodiment, the method comprises (a) incubating a sample including a target nucleic acid comprising a region of a wild type gene known to exhibit genetic variation with a primer pair; a first amplification blocking nucleic acid comprising a sequence that is the same as or complementary to at least two consecutive nucleotides of the region of a wild type gene known to exhibit genetic variation; and a second amplification blocking nucleic acid comprising a sequence complementary to at least two consecutive nucleotides of the first amplification blocking nucleic acid; (b) amplifying the target nucleic acid with a polymerase; thereby producing an amplification product and (c) detecting the amplification product to detect a nucleic acid with genetic variation.

The nucleic acid with genetic variation may be genomic DNA, genomic RNA, or a complementary DNA (cDNA). The genome refers to all genomic information. The genome includes genes and non-coding sequences. Genomic DNA refers to a genome consisting of DNA. Genomic RNA refers to a genome consisting of RNA. A cDNA refers to DNA synthesized from messenger RNA (mRNA) catalyzed by reverse transcriptase. The nucleic acid with genetic variation may include an allele, a Single Nucleotide Polymorphism (SNP), a mutation, or combinations thereof.

The sample may include a biological sample, DNA or RNA isolated from the sample or a fragment therefrom. The sample may include a sample derived from a virus or a biological organism. For example, the sample may be at least one selected from the group consisting of blood, saliva, urine, feces, a tissue, a cell and a biopsy material. The sample may be a stored biological sample or anything that includes DNA or RNA isolated therefrom. The sample may be stored according to a known method. The sample may be stored for at least one year, for example, in a range of about 1 to about 10 years (e.g., 2, 3, 4, 5, 6, 7, 8, or 9 years). The DNA or RNA may be derived from frozen stored tissue or formalin-fixed paraffin embedded tissue stored at room temperature. Methods of isolating DNA or RNA from a biological material are known in the art.

The primer pair can hybridize with a strand including the nucleic acid with genetic variation or a strand complementary to the same. The primer pair may be a genotype-specific primer pair which can hybridize with a nucleotide whose sequence is the same as or complementary to a nucleic acid with genetic variation. The genotype-specific primer pair may include a nucleotide whose sequence is the same as or complementary to at least two consecutive nucleotides of the first amplification blocking nucleic acid or the second amplification blocking nucleic acid.

The hybridization may be performed by a known method. For example, the hybridization may be performed by incubating the polynucleotide and the target nucleic acid in the presence of a buffer suitable for hybridization of nucleic acids. The hybridization may be performed at from about 0° C. to about 25° C., or at about 4° C. (e.g., 5° C., 10° C., 15° C., or 20° C.). The hybridization temperature may be selected appropriately according to the sequence and length of the selected polynucleotide and the target nucleic acid. The hybridization may be performed, for example, for about 1 hour to about 12 hours (overnight) (e.g., 2, 3, 4, 5, 6, 7, 8, 9, 10, or 11 hours).

The hybridization method includes incubating a product of the hybridization in the presence of a nucleic acid polymerase to amplify the nucleic acid with genetic variation.

The amplification method may be any known method of amplification. The amplification method may require a thermal cycling or may be performed under an isothermal condition. For example, the amplification method may include polymerase chain reaction (PCR), nucleic acid sequence-based amplification (NASBA), ligase chain reaction (LCR), strand displacement amplification (SDA), multiple displacement amplification (MDA), rolling circle amplification (RCA), or combinations thereof. The amplification method may also include an RNA amplification method, for example, reverse transcription (RT) or RT-PCR. "PCR" refers to a method of amplifying a target nucleic acid by using a polymerase and a primer pair binding specifically to the target nucleic acid. For example, the nucleic acid amplification repeats the steps of denaturation, annealing, and elongation. As used herein, "annealing" may be interchangeably used with the term "hybridization." The nucleic acid amplification may be DNA amplification or RNA amplification. The nucleic acid amplification may be real-time nucleic acid amplification. As used herein, "Real-Time PCR (RT-PCR)" refers to a method of real-time observation of the increase in PCR product per each PCR cycle. RT-PCR is used to analyze a given sample by detecting and quantifying a fluorescent material reacting with the PCR product.

Regarding the amplification, the amplification of a wild-type gene may be inhibited in the presence of the first amplification blocking nucleic acid and/or the second amplification blocking nucleic acid, and the nucleic acid with genetic variation may be selectively amplified.

The amplification method includes detecting a nucleic acid with genetic variation.

The amplification method enables selective detection of the nucleic acid with genetic variation.

In a further aspect of the present invention, there is provided another method of detecting a nucleic acid with genetic variation. The detection method comprises: (a) incubating a sample including a target nucleic acid comprising a region of a wild type gene known to exhibit genetic variation with a first primer pair, and a first amplification blocking nucleic acid, wherein the first amplification blocking nucleic acid comprises a sequence that is the same as or complementary to at least two consecutive nucleotides of the region of the wild type gene known to exhibit genetic variation; (b) amplifying the target nucleic acid with a nucleic acid polymerase to provide a first amplification product; (c) incubating the first amplification product with a second primer pair and a second amplification blocking nucleic acid, wherein the second amplification blocking nucleic acid comprises a sequence complementary to at least two consecutive nucleotides of the first amplification blocking nucleic acid; (d) amplifying the first amplification product with a nucleic acid polymerase to provide a second amplification product; and (e) detecting the second amplification product to detect a nucleic acid with genetic variation.

The first primer pair or the second primer pair can hybridize with a strand comprising a nucleic acid with genetic variation or a strand complementary to the same. The first primer pair may be a genotype-specific primer which can hybridize with a nucleotide whose sequence is the same as or complementary to the nucleic acid of a domain with genetic variation or a nucleotide complementary to the same. The genotype-specific primer pair may comprise a nucleotide whose sequence is the same as or complementary to at least two consecutive nucleotides of the first amplification blocking nucleic acid or the second amplification blocking nucleic acid.

Regarding the amplification, the amplification of a wild-type gene may be inhibited in the presence of the first amplification blocking nucleic acid and/or the second amplification blocking nucleic acid, and the nucleic acid with genetic variation may be selectively amplified.

The concentration of the first amplification blocking nucleic acid among the products of the second hybridization may be from about 0.02 nM to about 200 nM, about 0.02 nM to about 150 nM, about 0.02 nM to about 100 nM, about 0.02 nM to about 80 nM, about 0.02 nM to about 60 nM, about 0.02 nM to about 40 nM, about 0.02 nM to about 20 nM, about 0.2 nM to about 20 nM, about 0.5 nM to about 20 nM, about 1 nM to about 20 nM, or about 2 nM to about 20 nM.

The incubation of a sample including a target nucleic acid containing a region of a wild type gene known to exhibit genetic variation with a first primer pair, and a first amplification blocking nucleic acid may be an incubation of the sample with a first primer pair and a first amplification blocking nucleic acid without a second amplification blocking nucleic acid with a sequence complementary to the first amplification blocking nucleic acid.

A nucleic acid with genetic variation can be detected selectively by the detection. By detecting the nucleic acid with genetic variation, information necessary for the diagnosis of a disease can be provided.

EXAMPLES

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

Example 1

Preparation of a DNA Sample

Genomic DNA was extracted from white blood cells of a healthy adult and the H1975 cell line with L858R genotype of Epidermal growth factor receptor (EGFR) by using a QIAamp DNA mini kit (Qiagen).

The genomic DNA of white blood cells of a healthy adult and the genomic DNA of H1975 cell line with L858R genotype of EGFR were mixed to prepare DNA samples so that the weight % of the genomic DNA with L858R genotype relative to the total genomic DNA was 0%, 1%, 10%, and 100%.

Example 2

Effect of Genotype Detection by Using a Single Blocker

A quantitative polymerase chain reaction (qPCR) was performed using the DNA samples prepared in Example 1. The nucleotide sequences of the forward primer, the reverse primer, and the PNA blocker used in the qPCR are shown in Table 1 below.

TABLE 1

| | Nucleotide Sequence |
|---|---|
| forward primer | 5'-CCAGGAACGTACTGGTGAAAACAC-3' (SEQ ID NO: 1) |
| reverse primer | 5'-GCCTCCTTCTGCATGGTATTCTTT-3' (SEQ ID NO: 2) |
| PNA blocker | N-TTTGGGCTGGCCAAA-C (SEQ ID NO: 3) |

A qPCR was performed by mixing 50 ng of the genomic DNA prepared in Example 1, 200 nM of the forward primer, 200 nM of the reverse primer, 2 µM of the PNA blocker, and qPCR Premix (Exiqon).

A further qPCR was performed using 50 ng of the genomic DNA prepared in Example 1 and a PNAClamp™ EGFR mutation detection kit (PANAGENE) as a comparative group.

The qPCR was performed by incubating at 95° C. for 10 minutes, and then was performed repeatedly for 45 cycles wherein each cycle consisted of incubation at 95° C. for 10 seconds, at 70° C. for 20 seconds, at 63° C. (or 68° C.) for 30 seconds; at each of extension temperatures (63° C., 68° C., and 72° C.) for 30 seconds.

The difference between a crossing point (Cp) according to the qPCR and a Cp of genomic DNA, where the weight ratio of genomic DNA having the EGFR L858R genotype relative to the total genomic DNA is 0%, is represented by delta Cp (ΔCp), and the result is shown in Table 2 below.

TABLE 2

| | Ratio of genomic DNA with L858R genotype | Experimental Group | | | Comparative Group |
|---|---|---|---|---|---|
| | | Primer Annealing temperature/extension temperature | | | |
| | (%) | 63/63 | 63/68 | 63/72 | 63/72 |
| Cp | 0 | 31.44 | 31.47 | 29.52 | 32.5 |
| | 1 | 30.11 | 29.8 | 29.03 | 31.6 |
| | 10 | 27.16 | 27.01 | 27.21 | 29.3 |
| | 100 | 23.82 | 23.65 | 23.85 | 25.7 |
| delta Cp | 1 | 1.33 | 1.67 | 0.49 | 0.86 |
| | 10 | 4.28 | 4.46 | 2.31 | 3.24 |
| | 100 | 7.62 | 7.82 | 5.67 | 6.83 |

As shown in Table 2, the detection sensitivity of EGFR L858R genotype using a single blocker was confirmed to be about 10% the frequency of genetic variation (ΔCp>3 from the wild type genomic DNA).

Example 3

Effect of Genotype Detection Using Two Kinds of Complementary Blockers

A qPCR was performed by using two kinds of complementary blockers. The nucleotide sequences of the forward primer, the reverse primer, and the PNA blocker used in the qPCR are shown in Table 3 below.

A general primer is a primer specific to region without the L858R genotype, and a genotype-specific primer is a primer specific to region with the L858R genotype. A sense blocker is a blocker complementary to a sense strand which has the same nucleotide sequence as mRNA, and an anti-sense blocker is a blocker complementary to an anti-sense strand which has a nucleotide sequence complementary to mRNA. In addition, the underlined nucleotides in Table 3 represent the position of the L858R genotype.

A qPCR was performed by mixing 50 ng of the genomic DNA prepared in Example 1, 200 nM of the forward primer, 200 nM of the reverse primer, 2 μM of the PNA blocker, and qPCR Premix (Exiqon).

The qPCR was performed by incubating at 95° C. for 10 minutes and then was performed repeatedly for 45 cycles wherein each cycle consisted of incubation at 95° C. for 10 seconds, at 62° C. for 20 seconds, and at 60° C. for 60 seconds.

The Cp according to the qPCR was determined, and ΔCp calculated from the Cp is shown in Table 4 below.

TABLE 4

| | | Primer | | | |
|---|---|---|---|---|---|
| | | General Primer | | Genotype-specific primer | |
| a sense | an anti-sense | Ratio of genomic DNA with L858R genotype (%) | | | |
| blocker | blocker | 1 | 10 | 1 | 10 |
| 15-mer | 15-mer | Not detected | Not detected | Not detected | Not detected |
| 13-mer | 13-mer | Not detected | Not detected | Not detected | Not detected |
| 11-mer | 13-mer | 2.5 | 5.4 | 2.9 | 5.9 |
| 11-mer | 11-mer | 2.5 | 5.4 | 3.5 | 6.9 |
| 11-mer | 9-mer | 1.6 | 3.0 | 3.5 | 6.6 |
| 9-mer | 9-mer | 0.0 | 0.1 | 2.2 | 5.8 |
| • | 13-mer | 0.6 | 2.6 | 2.0 | 5.3 |
| 11-mer | • | 1.2 | 3.6 | 2.0 | 4.8 |
| • | 11-mer | −1.3 | −0.4 | 2.3 | 5.7 |
| • | 9-mer | −0.3 | −0.1 | 2.1 | 5.4 |
| • | 17-mer | 2.3 | 5.2 | 1.9 | 5.3 |
| • | • | −0.1 | 0.0 | 2.2 | 5.3 |

(*In Table 4, "•" indicates that a blocker is not included.)

As shown in Table 4, ΔCp increased when two complementary blockers were used as compared to when a single blocker of either a sense blocker or an anti-sense blocker

TABLE 3

| | | | | Nucleotide Sequence | |
|---|---|---|---|---|---|
| Primer | general primer | forward primer | | 5'-AGCCAGGAACGTACTGGTGA-3' | (SEQ ID NO: 4) |
| | | reverse primer | | 5'-GCCTCCTTCTGCATGGTATT-3' | (SEQ ID NO: 5) |
| | genotype-specific primer | forward primer | | 5'-AGCCAGGAACGTACTGGTGA-3' | (SEQ ID NO: 6) |
| | | reverse primer | | 5'-AAGATCACAGATTTTGGGCG-3' | (SEQ ID NO: 7) |
| PNA blocker | a sense blocker | 15-mer | | N-TTTGGGCTGGCCAAA-C | (SEQ ID NO: 8) |
| | | 13-mer | | N-TTGGGCTGGCCAA-C | (SEQ ID NO: 9) |
| | | 11-mer | | N-TGGGCTGGCCA-C | (SEQ ID NO: 10) |
| | | 9-mer | | N-GGGCTGGCC-C | (SEQ ID NO: 11) |
| | an anti-sense blocker | 17-mer | | N-GTTTGGCCAGCCCAAAA-C | (SEQ ID NO: 12) |
| | | 15-mer | | N-TTTGGCCAGCCCAAA-C | (SEQ ID NO: 13) |
| | | 13-mer | | N-TTGGCCAGCCCAA-C | (SEQ ID NO: 14) |
| | | 11-mer | | N-TGGCCAGCCCA-C | (SEQ ID NO: 15) |
| | | 9-mer | | N-GGCCAGCCC-C | (SEQ ID NO: 16) | was used, thus confirming that the detection sensitivity for EGFR L858R genotype was improved. In addition, ΔCp also increased when a genotype-specific primer was used as compared to when a general primer was used, thus showing the improvement in the detection sensitivity for EGFR L858R genotype.

Example 4

Effect of Genotype Detection Using Two Kinds of Complementary Blockers in Two Amplifications A qPCR was performed twice by using two kinds of complementary blockers. The nucleotide sequences of the forward primer, the reverse primer, and the PNA blocker used in the qPCR are shown in Table 5 below.

TABLE 5

| | | Nucleotide Sequence |
|---|---|---|
| Primer for the first qPCR | 1st forward primer | 5'-CTGGCATGAACATGAC CCTG-3' (SEQ ID NO: 17) |
| | 1st reverse primer | 5'-CTGACCTAAAGCCACCT CCTT-3' (SEQ ID NO: 18) |
| Primer for the second qPCR | 2nd forward primer | 5'-AGCCAGGAACGTACTGGTGA-3' (SEQ ID NO: 19) |
| | 2nd reverse primer | 5'-GCCTCCTTCTGCATGGTATT-3' (SEQ ID NO: 20) |
| PNA blocker | a sense blocker (17-mer) | N-TTTTGGGCTGGCCAAAC-C (SEQ ID NO: 21) |
| | an anti-sense blocker (17-mer) | N-GTTTGGCCAGCCCAAAA-C (SEQ ID NO: 22) |

The first qPCR product was diluted 1:100.

The second qPCR was performed by mixing 5 μL of the diluted first qPCR product, 50 nM of the second forward primer, 50 nM of the second reverse primer, 2 μM of the PNA blocker, and qPCR Premix (Exiqon) to a final volume of 20 μL. The second qPCR was performed by incubating at 95° C. for 10 minutes and then was performed repeatedly for 45 cycles wherein each cycle consisted of incubation at 95° C. for 10 seconds, at 65° C. for 20 seconds, and at 60° C. for 60 seconds.

The Cp according to the two qPCRs was determined, and ΔCp calculated from the Cp is shown in Table 6 below.

TABLE 6

| | | Cp | | | | | | ΔCp | |
|---|---|---|---|---|---|---|---|---|---|
| | | No. of template copies (no. of copies of genome with wild type EGFR: no. of copies of cell lines with L858R genotype of EGFR) | | | | | | | |
| the first qPCR | second qPCR | 1000:0 | 1000:10 | 1000:100 | 0:10 | 1000:10 | 1000:100 | | |
| • | • | 13.17 | 13.42 | 12.82 | 18.96 | −0.26 | 0.34 | | |
| • | a sense blocker | 18.98 | 17.81 | 15.40 | 19.35 | 1.17 | 3.58 | | |
| an anti-sense blocker | a sense blocker | 23.48 | 19.80 | 16.25 | 20.95 | 3.68 | 7.22 | | |
| a sense blocker | a sense blocker | 22.06 | 19.21 | 15.85 | 19.35 | 2.85 | 6.21 | | |
| • | an anti-sense blocker | 16.02 | 15.72 | 14.47 | 20.48 | 0.29 | 1.55 | | |
| a sense blocker | an anti-sense blocker | 23.27 | 20.05 | 16.46 | 20.99 | 3.22 | 6.81 | | |
| an anti-sense blocker | an anti-sense blocker | 20.34 | 20.08 | 15.59 | 19.99 | 0.25 | 4.75 | | |

(*In Table 6, "•" indicates that a blocker is not included.)

As shown in Table 6, ΔCp was increased when using a sense blocker in the first qPCR and using an anti-sense blocker in the second qPCR, and when using an anti-sense blocker in the first qPCR and using a sense blocker in the second qPCR, thus showing the improvement in the detection sensitivity for EGFR L858R genotype.

Example 5

Effect of Detection by Diluting the First qPCR Product when Using Two Kinds of Complementary Blockers in Two Amplifications qPCR was performed twice by using two kinds of complementary blockers, wherein the second qPCR was performed by diluting the first qPCR product.

The nucleotide sequences of the forward primer, the reverse primer, and the PNA blocker used in the qPCR are shown in Table 5 of Example 4.

The first qPCR was performed by mixing 50 ng of the genomic DNA prepared in Example 1, 250 nM of the first forward primer, 250 nM of the first reverse primer, 2 μM of the PNA blocker, and qPCR Premix (Exiqon). The first qPCR was performed by incubating at 95° C. for 10 minutes and then was performed repeatedly for 22 cycles, wherein each cycle consisted of incubation at 95° C. for 10 seconds, at 65° C. for 20 seconds, and at 60° C. for 60 seconds.

The second qPCR was performed by mixing the first qPCR product, 50 nM of the second forward primer, 50 nM of the second reverse primer, 2 μM of the PNA blocker, and qPCR Premix (Exiqon). The second qPCR was performed by incubating at 95° C. for 10 minutes and then was performed repeatedly for 45 cycles, wherein each cycle consisted of incubation at 95° C. for 10 seconds, at 65° C. for 20 seconds, and at 60° C. for 60 seconds. In the second qPCR, the first qPCR product was diluted so that the concentration of the PNA blocker used in the first qPCR can be adjusted to 500 nM, 100 nM, 20 nM, 2 nM, 0.2 nM, or 0.02 nM.

The Cp according to the two qPCRs was determined, and the Cp is shown in Table 7 below.

TABLE 7

| the first qPCR | the second qPCR | Concentration of PNA blocker used in the first qPCR in the second qPCR reactants (nM) | | | | | |
|---|---|---|---|---|---|---|---|
| | | 500 | 100 | 20 | 2 | 0.2 | 0.02 |
| a sense blocker | a sense blocker | 10.2 | 13.9 | 14.9 | 17.3 | 19.8 | 23.3 |
| a sense blocker | an anti-sense blocker | not detected | not detected | 16.2 | 18.3 | 20.7 | 23.7 |
| an anti-sense blocker | a sense blocker | not detected | not detected | not detected | 18.7 | 21.5 | 25.8 |
| an anti-sense blocker | an anti-sense blocker | 11.1 | 14.8 | 15.8 | 19 | 22.4 | 25.5 |

As shown in Table 7, ΔCp was increased when using a sense blocker in the first qPCR and using an anti-sense blocker in the second qPCR, and when using an anti-sense blocker in the first qPCR and using a sense blocker in the second qPCR, thus showing the improvement in the detection sensitivity for EGFR L858R genotype.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of detecting a nucleic acid with genetic variation, the method comprising:
   (a) incubating a sample comprising a target nucleic acid, wherein the target nucleic acid can be a nucleic acid with genetic variation or a wild-type nucleic acid differing from the nucleic acid with genetic variation, with
   a primer pair;
   a first amplification blocking nucleic acid comprising a sequence complementary to a sense strand of the wild-type nucleic acid, specific to the wild-type nucleic acid, and having a length in a range of 9 nucleotides to 13 nucleotides; and
   a second amplification blocking nucleic acid comprising a sequence complementary to an antisense strand of the wild-type nucleic acid, complementary to at least two consecutive nucleotides of the first amplification blocking nucleic acid, specific to the wild-type nucleic acid, and having a length of 11 nucleotides;
   wherein the first amplification blocking nucleic acid and the second amplification blocking nucleic acid each comprises a Peptide Nucleic Acid (PNA), Locked Nucleic Acid (LNA), Zip Nucleic Acid (ZNA), Bridged Nucleic Acid (BNA, nucleotide analogue, or combination thereof;
   (b) amplifying the target nucleic acid with a polymerase, thereby producing an amplification product,
   wherein amplification of the target nucleic acid is inhibited by the first amplification blocking nucleic acid and/or second amplification blocking nucleic acid if the target nucleic acid is the wild-type nucleic acid, but amplification of the target nucleic acid is not inhibited if the target nucleic acid is the nucleic acid with genetic variation;
   and
   (c) detecting the amplification product to detect the nucleic acid with genetic variation.

2. The method according to claim 1, wherein the target nucleic acid is genomic DNA, genomic RNA, or a complementary DNA (cDNA).

3. The method according to claim 1, wherein the region of the target nucleic acid known to have genetic variation comprises an allele, a Single Nucleotide Polymorphism (SNP), a mutation, or combination thereof.

4. The method according to claim 1, wherein the primer pair hybridizes with a strand comprising the nucleic acid with genetic variation or a strand complementary to the same.

5. The method according to claim 1, wherein the primer pair is hybridized with a nucleotide whose sequence is the same as or complementary to that of the nucleic acid with the region with genetic variation.

6. The method according to claim 1, wherein the first amplification blocking nucleic acid or the second amplification blocking nucleic acid is chemically modified.

7. The method according to claim 1, wherein the melting temperature of the first amplification blocking nucleic acid or the second amplification blocking nucleic acid is in a range of 50° C. to 80° C.

8. A method of detecting a nucleic acid with genetic variation, the method comprising:
   (a) incubating a sample comprising a target nucleic acid, wherein the target nucleic acid can be a nucleic acid with genetic variation or a wild-type nucleic acid differing from the nucleic acid with genetic variation, with
   a first primer pair and
   a first amplification blocking nucleic acid comprising a sequence complementary to a sense strand of the wild-type nucleic acid, specific to the wild-type nucleic acid, and having a length in the rage of 13 nucleotides to 24 nucleotides,
   wherein the first amplification blocking nucleic acid comprises a PNA, LNA, ZNA, BNA, nucleotide analogue, or combination thereof;
   (b) amplifying the target nucleic acid with a nucleic acid polymerase to provide a first amplification product, wherein amplification of the target nucleic acid is inhibited by the first amplification blocking agent if the target nucleic acid is the wild-type nucleic acid, but amplification of the target nucleic acid is not inhibited if the target nucleic acid is the nucleic acid with genetic variation;
   (c) incubating the first amplification product with
   a second primer pair and
   a second amplification blocking nucleic acid comprising a sequence complementary to an antisense strand of the wild-type nucleic acid, complementary to at least two consecutive nucleotides of the first amplification blocking nucleic acid, specific to the wild-type nucleic acid, and having a length in the range of 13 nucleotides to 24 nucleotides,
   wherein the second amplification blocking nucleic acid comprises a PNA, LNA, ZNA, BNA, nucleotide analogue, or combination thereof,
   wherein amplification of the target nucleic acid is inhibited by the second amplification blocking agent if the target nucleic acid is the wild-type nucleic acid, but amplification of the target nucleic acid is not inhibited if the target nucleic acid is the nucleic acid with genetic variation;
   (d) amplifying the first amplification product with a nucleic acid polymerase to provide a second amplification product; and
   (e) detecting the second amplification product to detect a nucleic acid with genetic variation.

9. The method according to claim 8, wherein the nucleic acid with genetic variation comprises an allele, a Single Nucleotide Polymorphism (SNP), a mutation or combinations thereof.

10. The method according to claim 8, wherein the first primer pair or the second primer pair can hybridize with a strand comprising a nucleic acid with genetic variation or a strand complementary to the same.

11. The method according to claim 8, wherein the first primer pair can hybridize with a nucleotide whose sequence is the same as or complementary to the nucleic acid of a domain with genetic variation or a nucleotide complementary to the same.

12. The method according to claim 8, wherein the first amplification blocking nucleic acid or the second amplification blocking nucleic acid is chemically modified.

13. The method according to claim 8, wherein the concentration of the first amplification blocking nucleic acid in the product of the second hybridization is in a range of 0.02 nM to 200 nM.

14. The method according to claim 8, wherein step (a) comprises incubating the sample with a first primer pair and a first amplification blocking nucleic acid without a second amplification blocking nucleic acid with a sequence complementary to the first amplification blocking nucleic acid.

\* \* \* \* \*

SEQUENCE LISTING

<160> NUMBER OF SEQ ID NOS: 22

<210> SEQ ID NO 1
<211> LENGTH: 24
<212> TYPE: DNA
<213> ORGANISM: Artificial Sequence
<220> FEATURE:
<223> OTHER INFORMATION: Synthetic (Forward primer)

<400> SEQUENCE: 1
ccaggaacgt actggtgaaa acac                                    24

<210> SEQ ID NO 2
<211> LENGTH: 24
<212> TYPE: DNA
<213> ORGANISM: Artificial Sequence
<220> FEATURE:
<223> OTHER INFORMATION: Synthetic (Reverse primer)

<400> SEQUENCE: 2
gcctccttct gcatggtatt cttt                                    24

<210> SEQ ID NO 3

```
<211> LENGTH: 15
<212> TYPE: DNA
<213> ORGANISM: Artificial Sequence
<220> FEATURE:
<223> OTHER INFORMATION: Synthetic (PNA blocker)

<400> SEQUENCE: 3
tttgggctgg ccaaa                                                        15

<210> SEQ ID NO 4
<211> LENGTH: 20
<212> TYPE: DNA
<213> ORGANISM: Artificial Sequence
<220> FEATURE:
<223> OTHER INFORMATION: Synthetic (Forward primer)

<400> SEQUENCE: 4
agccaggaac gtactggtga                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic (Reverse primer)

<400> SEQUENCE: 5
gcctccttct gcatggtatt                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic (Forward primer)

<400> SEQUENCE: 6
agccaggaac gtactggtga                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic (Reverse primer)

<400> SEQUENCE: 7
aagatcacag attttgggcg                                                   20

<210> SEQ ID NO 8
<211> LENGTH: 15
<212> TYPE: DNA
<213> ORGANISM: Artificial Sequence
<220> FEATURE:
<223> OTHER INFORMATION: Synthetic (PNA sense blocker)

<400> SEQUENCE: 8
tttgggctgg ccaaa                                                        15

<210> SEQ ID NO 9
<211> LENGTH: 13
<212> TYPE: DNA
<213> ORGANISM: Artificial Sequence
<220> FEATURE:
<223> OTHER INFORMATION: Synthetic (PNA sense blocker)

<400> SEQUENCE: 9
```

-continued

```
ttgggctggc caa                                                         13

<210> SEQ ID NO 10
<211> LENGTH: 11
<212> TYPE: DNA
<213> ORGANISM: Artificial Sequence
<220> FEATURE:
<223> OTHER INFORMATION: Synthetic (PNA sense blocker)

<400> SEQUENCE: 10
tgggctggcc a                                                           11

<210> SEQ ID NO 11
<211> LENGTH: 9
<212> TYPE: DNA
<213> ORGANISM: Artificial Sequence
<220> FEATURE:
<223> OTHER INFORMATION: Synthetic (PNA sense blocker)

<400> SEQUENCE: 11 gggctggcc                                                               9

<210> SEQ ID NO 12
<211> LENGTH: 17
<212> TYPE: DNA
<213> ORGANISM: Artificial Sequence
<220> FEATURE:
<223> OTHER INFORMATION: Synthetic (PNA antisense blocker)

<400> SEQUENCE: 12
gtttggccag cccaaaa                                                     17

<210> SEQ ID NO 13
<211> LENGTH: 15
<212> TYPE: DNA
<213> ORGANISM: Artificial Sequence
<220> FEATURE:
<223> OTHER INFORMATION: Synthetic (PNA antisense blocker)

<400> SEQUENCE: 13
tttggccagc ccaaa                                                       15

<210> SEQ ID NO 14
<211> LENGTH: 13
<212> TYPE: DNA
<213> ORGANISM: Artificial Sequence
<220> FEATURE:
<223> OTHER INFORMATION: Synthetic (PNA antisense blocker)

<400> SEQUENCE: 14
ttggccagcc caa                                                         13

<210> SEQ ID NO 15
<211> LENGTH: 11
<212> TYPE: DNA
<213> ORGANISM: Artificial Sequence
<220> FEATURE:
<223> OTHER INFORMATION: Synthetic (PNA antisense blocker)

<400> SEQUENCE: 15
tggccagccc a                                                           11

<210> SEQ ID NO 16
<211> LENGTH: 9
<212> TYPE: DNA
```

```
<213> ORGANISM: Artificial Sequence
<220> FEATURE:
<223> OTHER INFORMATION: Synthetic (PNA antisense blocker)

<400> SEQUENCE: 16 ggccagccc                                                                          9

<210> SEQ ID NO 17
<211> LENGTH: 20
<212> TYPE: DNA
<213> ORGANISM: Artificial Sequence
<220> FEATURE:
<223> OTHER INFORMATION: Synthetic (Forward primer)

<400> SEQUENCE: 17
ctggcatgaa catgaccctg                                                             20

<210> SEQ ID NO 18
<211> LENGTH: 21
<212> TYPE: DNA
<213> ORGANISM: Artificial Sequence
<220> FEATURE:
<223> OTHER INFORMATION: Synthetic (Reverse primer)

<400> SEQUENCE: 18
ctgacctaaa gccacctcct t                                                           21

<210> SEQ ID NO 19
<211> LENGTH: 20
<212> TYPE: DNA
<213> ORGANISM: Artificial Sequence
<220> FEATURE:
<223> OTHER INFORMATION: Synthetic (Forward primer)

<400> SEQUENCE: 19
agccaggaac gtactggtga                                                             20

<210> SEQ ID NO 20
<211> LENGTH: 20
<212> TYPE: DNA
<213> ORGANISM: Artificial Sequence
<220> FEATURE:
<223> OTHER INFORMATION: Synthetic (Reverse primer)

<400> SEQUENCE: 20
gcctccttct gcatggtatt                                                             20

<210> SEQ ID NO 21
<211> LENGTH: 17
<212> TYPE: DNA
<213> ORGANISM: Artificial Sequence
<220> FEATURE:
<223> OTHER INFORMATION: Synthetic (PNA sense blocker)

<400> SEQUENCE: 21
ttttgggctg gccaaac                                                                17

<210> SEQ ID NO 22
<211> LENGTH: 17
<212> TYPE: DNA
```

```
<213> ORGANISM: Artificial Sequence
<220> FEATURE:
<223> OTHER INFORMATION: Synthetic (PNA antisense blocker)

<400> SEQUENCE: 22
gtttggccag cccaaaa                                                17
```